United States Patent
Cook et al.

(10) Patent No.: US 10,508,067 B2
(45) Date of Patent: Dec. 17, 2019

(54) PROCESS FOR DEHYDROHALOGENATION OF HALOGENATED ALKANES

(71) Applicant: HONEYWELL INTERNATIONAL INC., Morris Plains, NJ (US)

(72) Inventors: George R. Cook, Buffalo, NY (US); Haluk Kopkalli, Staten Island, NY (US); Stephen A. Cottrell, Baton Rouge, LA (US); Yuon Chiu, Denville, NJ (US); Peter Scheidle, Wheatfield, NY (US); Daniel C. Merkel, Orchard Park, NY (US)

(73) Assignee: Honeywell International Inc., Morris Plains, NJ (US)

( * ) Notice: Subject to any disclaimer, the term of this patent is extended or adjusted under 35 U.S.C. 154(b) by 0 days.

(21) Appl. No.: 15/888,331

(22) Filed: Feb. 5, 2018

(65) Prior Publication Data

US 2018/0327340 A1    Nov. 15, 2018

Related U.S. Application Data

(62) Division of application No. 13/863,670, filed on Apr. 16, 2013, now Pat. No. 9,884,796, which is a division of application No. 12/770,217, filed on Apr. 29, 2010, now abandoned.

(51) Int. Cl.
   *C07C 17/23*    (2006.01)
   *C07C 17/25*    (2006.01)

(52) U.S. Cl.
   CPC .............. *C07C 17/23* (2013.01); *C07C 17/25* (2013.01)

(58) Field of Classification Search
   CPC ....................................................... C07C 17/23
   See application file for complete search history.

(56) References Cited

U.S. PATENT DOCUMENTS

| | | |
|---|---|---|
| 5,573,654 A | 11/1996 | Cheburkov et al. |
| 6,031,141 A | 2/2000 | Mallikarjuna et al. |
| 6,369,284 B1 | 4/2002 | Nappa et al. |
| 6,380,446 B1 | 4/2002 | Drew et al. |
| 7,560,602 B2 | 7/2009 | Van Der Puy et al. |
| 2005/0070746 A1 | 3/2005 | Tung et al. |
| 2008/0255396 A1 | 10/2008 | Rao et al. |
| 2009/0099396 A1* | 4/2009 | Mukhopadhyay ...... C07C 17/21 570/160 |
| 2009/0234165 A1 | 9/2009 | Chiu et al. |
| 2010/0022809 A1 | 1/2010 | Cottrell et al. |
| 2011/0190554 A1 | 8/2011 | Pigamo et al. |

FOREIGN PATENT DOCUMENTS

| | | |
|---|---|---|
| WO | 2008075017 A2 | 6/2008 |
| WO | 2009003084 A1 | 12/2008 |
| WO | 2009030439 A2 | 3/2009 |
| WO | 2009125199 A2 | 10/2009 |
| WO | 2009125200 A2 | 10/2009 |
| WO | 2009125201 A2 | 10/2009 |
| WO | 2010029240 A1 | 3/2010 |

* cited by examiner

*Primary Examiner* — Shawquia Jackson
(74) *Attorney, Agent, or Firm* — Faegre Baker Daniels LLP

(57) ABSTRACT

A process for the manufacture of halogenated olefins in semi-batch mode by dehydrohalogenation of halogenated alkanes in the presence of an aqueous base such as KOH which simultaneously neutralizes the resulting hydrogen halide. During the process, aqueous base is continuously added to the haloalkane which results in better yields, lower by-product formation and safer/more controllable operation.

11 Claims, 1 Drawing Sheet

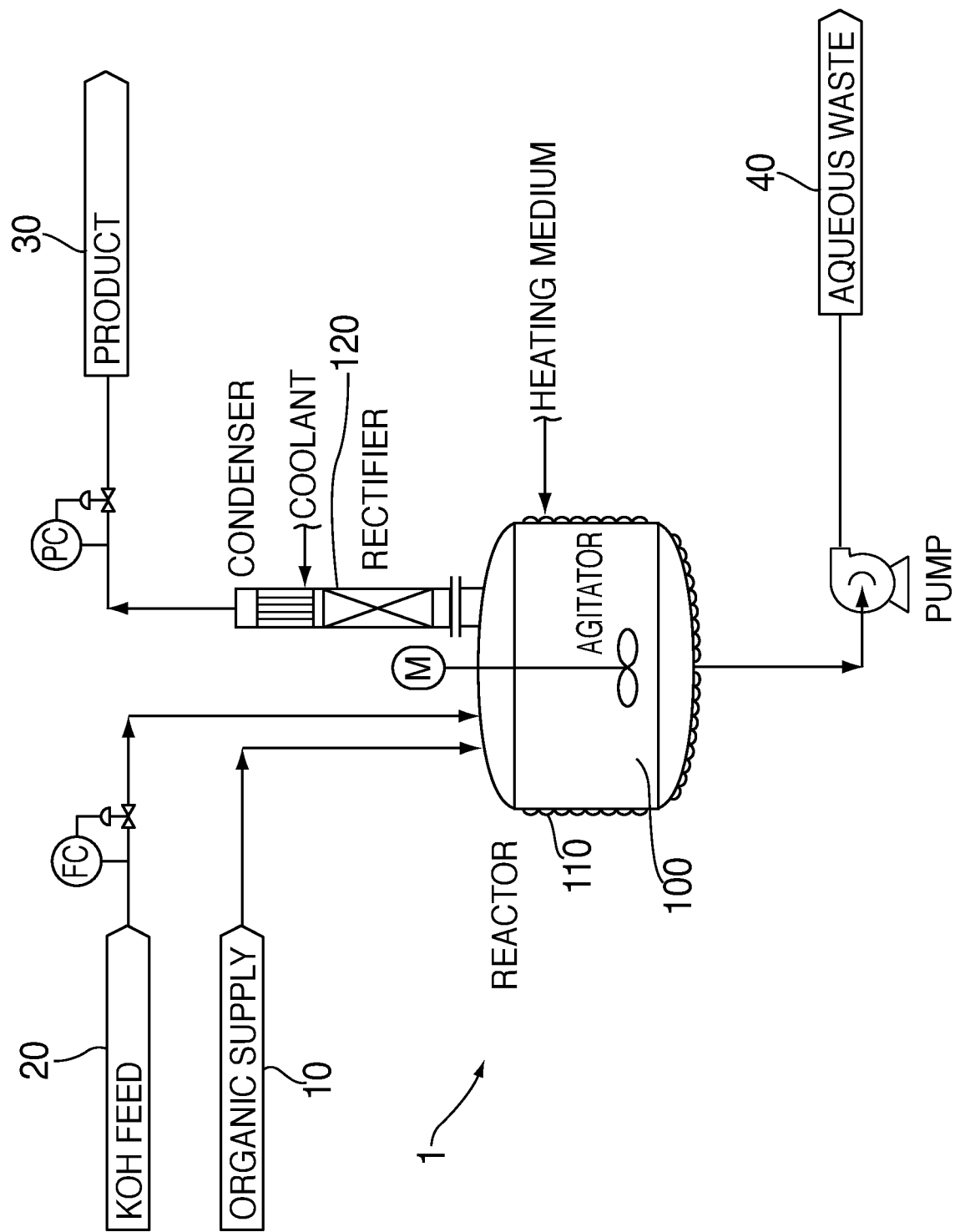

PROCESS FOR DEHYDROHALOGENATION OF HALOGENATED ALKANES

CROSS REFERENCE TO RELATED APPLICATIONS

This application is a division of U.S. application Ser. No. 13/863,670, filed Apr. 16, 2013, which application is a division of U.S. application Ser. No. 12/770,217, filed Apr. 29, 2010 (now abandoned).

BACKGROUND

Field of Invention

This invention relates to processes for producing hydrofluoroolefins. More particularly, this process relates to processes for producing hydrofluoroolefins via dehydrohalogenation.

Description of Related Art

Certain hydrofluoroolefins (HFOs), such as HFO-1225zc, HFO-1234yf and HFO-1234ze, have zero ozone depletion potential and have very low global-warming potential such that they are desirable replacement for hydrofluorocarbons (HFCs) such as HFC-134a and HFC-245fa in applications such as refrigeration, foam blowing, etc.

One method for synthesizing hydrofluoroolefins involves dehydrohalogenation of a halogenated alkane, such as hydrofluorocarbons and hydrochlorofluorocarbons (HCFCs). Such dehydrohalogenation reactions can occur as a liquid or gas phase reaction.

For liquid phase dehydrohalogenation reactions, one method involves reacting the HCFC or HFC in the presence of a KOH solution which simultaneously neutralizes the HF or HCl according to the reactions below:

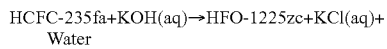
HCFC-235fa+KOH(aq)→HFO-1225zc+KCl(aq)+ Water

HFC-236fa+KOH(aq)→HFO-1225zc+KF(aq)+Water

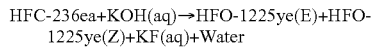
HFC-236ea+KOH(aq)→HFO-1225ye(E)+HFO-1225ye(Z)+KF(aq)+Water

HFC-245eb+KOH(aq)→HFO-1234yf+KF(aq)+Water

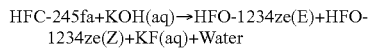
HFC-245fa+KOH(aq)→HFO-1234ze(E)+HFO-1234ze(Z)+KF(aq)+Water

Conventionally, such liquid phase reactions are performed as a batch process wherein the reactants are charged into a batch reactor without regard to their order of addition. Typically, the charged reactants are allowed to react for a period of time followed by recovery of the product. This mode of operation results in long batch times as well as large amounts of moisture in the crude product. Hence there is a need to design a more economical and more effective means of carrying out the above reactions.

SUMMARY OF THE INVENTION

It has been discovered that for liquid phase dehydrohalogenation reactions involving an aqueous base, the order in which the reactants are charged into a reactor affects the product yield and composition. Moreover, it has been discovered that limiting the amount of aqueous based in the reaction admixture can increase the product yield and selectivity.

Accordingly, provided is a process for preparing a hydrofluoroolefin comprising the following steps: (a) introducing an alkali-metal hydroxide feed stream into a reactor precharged with at least one halogenated propane having a structure according to Formula I:

$$C_3F_xCl_yH_{8-x-y} \qquad \text{(Formula I)}$$

wherein x is 5 or 6 and y is 0 or 1, provided that x+y is 6; (b) reacting, in a liquid phase, said halogenated propane with said an aqueous base in said reactor to produce a halogenated propene having a structure according to Formula II:

$$C_3F_{z-1}Cl_yH_{7-z} \qquad \text{(Formula I)}$$

wherein z is x−1; and (c) removing at least a portion of said halogenated propene from said reactor as a vapor product stream, wherein steps (a), (b), and (c) are at least partially performed simultaneously.

Also provided is a process for dehydrohalogenating a compound comprising: (a) providing a reaction admixture comprising potassium hydroxide and a halogenated propane having a degree of halogenation of M; (b) reacting said potassium hydroxide with said halogenated propane to form a halogenated propene having a degree of halogenation of M−1.

BRIEF DESCRIPTION OF THE DRAWING

FIG. 1 shows a dehydrohalogenation system according to a preferred embodiment of the present invention.

DETAILED DESCRIPTION OF PREFERRED EMBODIMENTS OF THE INVENTIONS

This invention provides for a more effective method for dehydrofluorination of certain hydrofluorocarbons and hydrochlorofluorocarbons in the presence of aqueous base. In certain preferred embodiments, this method is a semi-batch process having the following general steps: (a) precharging all or a portion of an organic reactant, e.g., unsaturated starting material, into a reactor, such as a stirred tank reactor; (b) optionally heating the contents of the reactor to a desired reaction temperature; (c) forming a reaction admixture by continuously adding an aqueous base to the organic reactant, wherein the aqueous base is continuously added during a reaction cycle so it is consumed immediately (or almost immediately) so as not to build up a concentration of aqueous base in the admixture (d) reacting the organic reactant with the aqueous base to produce a vapor phase dehydrohalogenated product; (e) separating the resulting vapor phase product from the reaction admixture; and (f) passing the reaction vapors through a rectifying column and a condenser while (1) refluxing unreacted starting material and moisture back to the reactor (2) allowing a predominantly pure product to leave the system as a vapor. At the end of the reaction cycle when the majority of the organic reactant is exhausted, the reactor contents may be heated further to drive off additional organic from the aqueous phase followed by draining the reactor to prepare for the next batch.

In certain preferred embodiments, the organic reactant comprises a halogenated propane, preferably a hydrofluorocarbon or a hydrochlorofluorocarbon. In certain preferred embodiments, the halogenated propane has a structure according to Formula I:

$$C_3F_xCl_yH_{8-x-y} \quad \text{(Formula I)}$$

wherein x is 5 or 6 and y is 0 or 1, provided that x+y is ≤6. Examples of such halogenated propanes include 1-chloro-1,1,3,3,3-pentafluoropropane (HCFC-235fa), 1,1,1,2,3-pentafluoropropane (HFC-245eb), 1, 1, 1, 2, 3, 3-hexafluoropropane (HFC-236ea), 1,1,1,3,3,3-hexafluoropropane (HFC-236fa), and 1,1,1,3,3-pentafluoropropane (HFC-245fa).

In certain preferred embodiments, the aqueous base is an alkali-metal hydroxide, such as KOH. The strength of the base is not particularly limited, but preferably is about 10-50%. For embodiments in which the organic reactant comprises HFC-236 the strength of the aqueous KOH is preferably about 30-40%. For embodiments in which the organic reactant comprises HFC-245, the strength of the aqueous KOH is preferably about 40-50%.

Preferably, the aqueous base is added to the organic reactant as a continuous feed stream.

Preferably, the reaction is performed at a temperature of about 40 to about 75° C., and more preferably about 50 to about 60° C.

Turning to FIG. 1, shown is a semi-batch dehydrohalogenation system 1 according to a preferred embodiment of the invention. Here, an organic reactant 10 is charged into a stir tank reactor 100. During or subsequent to the charging, the temperature of the reactor is controlled via the tank heating/cooling medium 110. After at least a majority, and preferably all, of an organic reactant feed for a reaction cycle is charged into reactor 100, a KOH feed stream 20 is introduced into the reactor to initiate a liquid phase dehydrohalogenation reaction. The vapor phase product stream (comprising a hydrofluoroolefin reaction product derived from the organic reactant and optionally unreacted organic reactant and moisture) exits the reactor 100 via rectifier/condenser 120. Here, unreacted organic reactant and moisture reflux back into the reactor 100, while the desired hydrofluoroolefin is removed as a product stream 30. At the end of the reaction cycle, the aqueous waste 40 is removed from the reactor 100.

The benefit of such an operation is reduced batch cycle time due to continuous withdrawal of product while returning reactant thereby maintaining conditions favorable to driving the reaction to the right side of the chemical equation. That is, by continuously reducing the concentration of the product, the reaction kinetics are favorably impacted. An additional benefit is a reduction in the amount of water that leaves the reactor since any moisture in the crude product must be removed prior to subsequent processing. Another benefit is an improved yield due to lower instantaneous concentration of the aqueous base in contact with a more fragile molecule (the halogenated alkane and/or the halogenated olefin). Yet another benefit is a safer operation since of the two reactants, the aqueous base is the limiting reactant and hence the energy stored within the reaction system is minimized.

EXAMPLES

The following non-limiting examples are given to provide a better understanding of the claimed invention.

Comparative Example 1: HFO-1225zc from HCFC-235fa

A 10 gallon jacketed metal reactor equipped with an agitator, rectifying column, and condenser (to reflux unreacted organic material back to the reactor) were prepared to run a dehydrohalogenation reaction. The reaction being studied was the dehydrochlorination of 1-chloro-1,1,3,3,3-pentafluoropropane (HCFC-235fa) to produce 1,1,3,3,3-pentafluoropropene (HFO-1225zc). For a first experiment, the reactor was charged with 35.2 lbs of 38 wt % KOH solution and 0.4 lbs of a phase transfer catalyst. The mixture was then agitated at 420 RPM and heated to 98-100° C. About 27.1 lbs of crude organic stream containing 65% HCFC-235fa was added over 6 hours. The reactor pressure rose to about 200 psig and some product was removed from the top of condenser as it was formed according to the target temperature at the top of the column indicating presence of 1,1,3,3,3-pentafluoropropene. The overhead material was dried using a desiccant and collected in a dry-ice trap. This approach did not work as the high concentration of high pH material (KOH) decomposed the organic producing acetates and formates which stayed in the aqueous layer in the reactor. The overall yield organic recovered overhead was about 30%. A second experiment was run similarly with comparable results.

Example 1: HFO-1225zc from HCFC-235fa

The same equipment, reactants, and operating conditions were used as described in Comparative Example 1, but for Example 1 the order of addition was changed. The 27.1 lbs of crude organic containing 65% HCFC-235fa organic was put into the reactor first, and heated to the reaction temperature. The rectifying column was then started at total reflux. Next, 38% KOH solution and phase transfer catalyst were fed into the reactor continuously over several hours. The dehydrochlorination reaction proceeded consuming the KOH as it was added leading to a lower pH system, which did not decompose the reactants and product, and allowed recovery of the product overhead.

The results of this experiment were better than those of comparative example 1. More particularly, the reaction demonstrated a 85% conversion of HCFC-235fa and 77% selectivity to HFO-1225zc.

Comparative Example 2: HFO-1234ze from HFC-245fa

This reaction was run in a semi-batch mode. About 12500 lbs of 45% KOH was charged to a 2000 gallon agitated reaction vessel. The reactor was also equipped with a rectifying column and condenser. The reactor was then heated to about 60° C. After the desired temperature was achieved, 8800 lbs of HFC-245fa was fed to the reactor over a several hour period to produce a desired HFO-1234ze product by dehydrofluorination. As the reaction was initiated the pressure in the reactor was allowed to rise to about 100 psig where it was maintained by use of a pressure control valve. Crude HFO-1234ze exiting the top of the condenser was dried with a desiccant and collected in a chilled tank. The rectifying column and condenser continuously refluxed unreacted 245fa back to the reactor for further processing during the run. After the desired amount of HFC-245fa was fed a material balance was performed. The organic yield was only 65%. A dark color was observed in the spent KOH stream at the end of the batch. Analysis of the spent KOH revealed high levels of acetates and formates, indicating a large portion of the HFC-245fa reacted to form undesirable by-products.

Example 2: HFO-1234ze from HFC-245fa

The same equipment from Comparative Example 2 was used in Example 2. The reaction was run in a semi-batch mode. About 12500 lbs of 245fa was charged to the reaction vessel. The reactor was then heated to about 60° C. After the desired temperature was achieved, 12000 lbs of 45% KOH was fed to the reactor over a several hour period to produce a desired HFO-1234ze product by dehydrofluorination. As the reaction was initiated the pressure in the reactor was allowed to rise to about 80 psig where it was maintained by use of a pressure control valve. Crude HFO-1234ze exiting the top of the condenser was dried with a desiccant and collected in a chilled tank. The rectifying column and condenser continuously refluxed unreacted 245fa back to the reactor for further processing during the run. After the desired amount of 45% KOH was fed a material balance was performed. The organic yield was 95%, which is quite acceptable for an economical process. Only a slight discoloration was observed in the spent KOH stream at the end of batch. Analysis of the spent KOH revealed low levels of acetates and formates, indicating that only a small portion of the HFC-245fa reacted to form undesirable products.

Comparative Example 3: HFO-1225ye from HFC-236ea

The reaction is run in a semi-batch mode. About 12500 lbs of 45% KOH is charged to a 2000 gallon agitated reaction vessel. The reactor is also equipped with a rectifying column and condenser. The reactor is then heated to about 60° C. After the desired temperature is achieved, 10200 lbs of HFC-236ea is fed to the reactor over a several hour period to produce a desired HFO-1225ye product by dehydrofluorination. As the reaction is initiated the pressure in the reactor is allowed to rise to about 100 psig where it is maintained by use of a pressure control valve. Crude HFO-1225ye exiting the top of the condenser is dried with a desiccant and collected in a chilled tank. The rectifying column and condenser continuously reflux unreacted 236ea back to the reactor for further processing during the run. After the desired amount of 236ea is fed a material balance is performed. The organic yield is only 65%, which is not an acceptable value for an economical process. A dark color is observed in the spent KOH stream at the end of the batch. Analysis of the spent KOH reveals high levels of acetates and formates, indicating a large portion of the HFC-236ea reacts to form undesirable products.

Example 3: HFO-1225ye from HFC-236ea

The same equipment from Comparative Example 3 is used in Example 3. The reaction is run in a semi-batch mode. About 14400 lbs of 236ea is charged to the reaction vessel. The reactor is then heated to about 60° C. After the desired temperature is achieved, 12000 lbs of 45% KOH is fed to the reactor over a several hour period to produce a desired HFO-1225ye product by dehydrofluorination. As the reaction is initiated the pressure in the reactor is allowed to rise to about 100 psig where it is maintained by use of a pressure control valve. Crude HFO-1225ye exiting the top of the condenser is dried with a desiccant and collected in a chilled tank. The rectifying column and condenser continuously reflux unreacted 236ea back to the reactor for further processing during the run. After the desired amount of 45% KOH is fed a material balance is performed. The organic yield is 95%, which is quite acceptable for an economical process. Only a slight discoloration is observed in the spent KOH stream at the end of batch. Analysis of the spent KOH reveals low levels of acetates and formates, indicating that only a small portion of the HFC-236ea reacts to form undesirable products.

Comparative Example 4: HFO-1234yf from HFC-245eb

The reaction is run in a semi-batch mode. About 12500 lbs of 45% KOH is charged to a 2000 gallon agitated reaction vessel. The reactor is also equipped with a rectifying column and condenser. The reactor is then heated to about 60° C. After the desired temperature is achieved, 8800 lbs of HFC-245eb is fed to the reactor over a several hour period to produce a desired HFO-1234yf product by dehydrofluorination. As the reaction is initiated the pressure in the reactor is allowed to rise to about 100 psig where it is maintained by use of a pressure control valve. Crude HFO-1234yf exiting the top of the condenser is dried with a desiccant and collected in a chilled tank. The rectifying column and condenser continuously reflux unreacted 245eb back to the reactor for further processing during the run. After the desired amount of 245eb is fed a material balance is performed. The organic yield is only 65%, which is not an acceptable value for an economical process. A dark color is observed in the spent KOH stream at the end of the batch. Analysis of the spent KOH reveals high levels of acetates and formates, indicating a large portion of the HFC-245eb reacts to form undesirable products.

Example 4: HFO-1234yf from HFC-245eb

The same equipment from Comparative Example 4 is used in Example 4. The reaction is run in a semi-batch mode. About 12500 lbs of 245eb is charged to the reaction vessel. The reactor is then heated to about 60° C. After the desired temperature is achieved, 12000 lbs of 45% KOH is fed to the reactor over a several hour period to produce a desired HFO-1234yf product by dehydrofluorination. As the reaction is initiated the pressure in the reactor is allowed to rise to about 100 psig where it is maintained by use of a pressure control valve. Crude HFO-1234yf exiting the top of the condenser is dried with a desiccant and collected in a chilled tank. The rectifying column and condenser continuously reflux unreacted 245eb back to the reactor for further processing during the run. After the desired amount of 45% KOH is fed a material balance is performed. The organic yield is 95%, which is quite acceptable for an economical process. Only a slight discoloration is observed in the spent KOH stream at the end of batch. Analysis of the spent KOH reveals low levels of acetates and formates, indicating that only a small portion of the HFC-245eb reacts to form undesirable products.

Comparative Example 5: HFO-1225zc from HFC-236fa

A 10 gallon jacketed metal reactor equipped with an agitator, rectifying column, and condenser (to reflux unreacted organic material back to the reactor) is prepared to run a dehydrohalogenation reaction. The reaction being studied is the dehydrofluorination of 1-chloro-1,1,3,3,3-pentafluoropropane (HCF236fa) to produce 1,1,3,3,3-pentafluoropropene (HFO1225zc). For Exp#1, the reactor is charged with 36 lbs of 45 wt % KOH solution and 0.4 lbs of a phase transfer catalyst. The mixture is then agitated at 350 RPM and heated to 90° C. 30 lbs of 98% pure HFC236fa is added over 6 hours. The reactor pressure rises to about 200 psig and some product is removed from the top of condenser as it is formed according to the target temperature at the top of the column, indicating the presence of 1,1,3,3,3-pentafluoropropene. The overhead material is dried using a desiccant and collected in a dry-ice trap. This approach does not work as the high concentration of high pH material (KOH) decomposes the organic, producing acetates and formates which stay in the aqueous layer in the reactor. The overall yield organic recovered overhead is about 35%.

Example 5: HFO-1225zc from HFC-236Fa

The same equipment, reactants, and operating conditions are used as described in Comparative Example 5, but for Exp#2 the order of addition is reversed. The 30 lbs of 236fa is put into the reactor first, and heated to the reaction temperature. The rectifying column is then started at total reflux. Next, 45% KOH solution and phase transfer catalyst are fed into the reactor continuously over several hours. The dehydrofluorination reaction commences consuming the KOH as it is added leading to a lower pH system, which does not decompose the reactants and product, and allows recovery of the product overhead. Results of Exp#2 are much better than Exp#1 with 80% conversion of HCFC236fa and 90% selectivity to 1225zc.

What is claimed is:

1. A process for preparing a halogenated propene comprising:
   a. introducing an alkali-metal hydroxide feed stream into a reactor charged with at least one halogenated propane having a structure according to Formula I:

$C_3F_xCl_yH_{8-x-y}$ (Formula I)

wherein x is 5 or 6 and y is 0 or 1, provided that x+y is ≤6;
   b. reacting, in a liquid phase, said at least one halogenated propane with said alkali-metal hydroxide in said reactor to produce a halogenated propene having a structure according to Formula II:

$C_3F_{z-1}H_{7-z}$ (Formula II)

wherein z is x−1; and
   c. removing at least a portion of said halogenated propene from said reactor as a vapor product stream,
   wherein steps (a), (b), and (c) are at least partially performed simultaneously.

2. The process of claim 1, wherein said halogenated propane is HFC-236ea and said halogenated propene is HFO-1225ye.

3. The process of claim 1, wherein said halogenated propane is HFC-245eb and said halogenated propene is HFO-1234yf.

4. The process of claim 1, further comprising refluxing at least a portion of unreacted halogenated propane in said vapor product stream back to said reactor.

5. The process of claim 4, further comprising refluxing water in said vapor product stream back to said reactor.

6. The process of claim 1, wherein said reacting occurs at a temperature of about 40 to about 75° C.

7. The process of claim 6, wherein said reacting occurs at a temperature of about 50 to about 60° C.

8. The process of claim 1, wherein said alkali metal hydroxide is potassium hydroxide.

9. The process of claim 8, wherein potassium hydroxide is present in a concentration of about 10 to about 50 wt. %.

10. The process of claim 1, wherein said halogenated propane is HFC-245fa and said halogenated propene is HFO-1234ze.

11. The process of claim 1, wherein said alkali metal hydroxide is sodium hydroxide.

* * * * *